United States Patent [19]
Didillion et al.

[11] Patent Number: 5,866,746
[45] Date of Patent: Feb. 2, 1999

[54] CATALYTIC DEHYDROISOMERIZATION OF $C_4$-$C_5$ N-PARAFFINS

[75] Inventors: Blaise Didillion; Christine Travers, both of Rueil Malmaison; Jean-Pierre Burzynski, Sainte-Foy-les Lyon, all of France

[73] Assignee: Institut Francais du Petrole, France

[21] Appl. No.: 728,424

[22] Filed: Oct. 10, 1996

Related U.S. Application Data

[63] Continuation-in-part of Ser. No. 488,296, Jun. 7, 1995, abandoned, which is a continuation-in-part of Ser. No. 430,449, Apr. 28, 1995, abandoned.

[30] Foreign Application Priority Data

Apr. 28, 1994 [FR] France .................................. 94/05.294

[51] Int. Cl.[6] ........................................ C07C 5/333
[52] U.S. Cl. .................... 585/661; 585/660; 585/671; 585/654
[58] Field of Search .................... 585/660, 661, 585/671, 654; 502/38

[56] References Cited

U.S. PATENT DOCUMENTS

| | | | |
|---|---|---|---|
| 2,346,657 | 4/1944 | Bloch et al. | 585/671 |
| 2,389,406 | 11/1945 | Bloch et al. | 585/671 |
| 3,679,602 | 7/1972 | Pollitzer | 585/671 |
| 3,730,958 | 5/1973 | Myers | 585/671 |
| 4,433,190 | 2/1984 | Sikkenga et al. | 585/660 |
| 4,503,282 | 3/1985 | Sikkenga | 585/671 |
| 4,762,960 | 8/1988 | Imai | 585/660 |
| 5,143,886 | 9/1992 | Iezzi et al. | 502/242 |
| 5,198,597 | 3/1993 | O'Young et al. | 585/671 |

FOREIGN PATENT DOCUMENTS

| | | |
|---|---|---|
| 1331318 | 9/1973 | United Kingdom . |
| 2 246 524 | 2/1992 | United Kingdom . |

*Primary Examiner*—Walter D. Griffin
*Attorney, Agent, or Firm*—Millen, White, Zelano & Branigan, P.C.

[57] ABSTRACT

The present invention concerns, in the dehydroisomerization of at least one $C_4$–$C_5$ n-paraffin, preferably n-butane, the use of a catalyst comprising a refractory oxide based support, preferably an alumina, at least one precious metal from group VIII, preferably platinum or palladium, optionally at least one element from group IVB such as titanium or zirconium, preferably titanium, optionally at least one element from the group formed by germanium, tin, lead, rhenium, tungsten and indium, and optionally at least one halogen such as chlorine. The present invention also concerns the regeneration of this catalyst.

10 Claims, No Drawings

CATALYTIC DEHYDROISOMERIZATION OF C₄-C₅ N-PARAFFINS

This application is a continuation-in-part of application Ser. No. 08/488,296, filed Jun. 7, 1995, now abandoned, which is a continuation-in-part of application Ser. No. 08/430,449 filed Apr. 28, 1995, now abandoned.

The present invention concerns the use of a particular catalyst in the dehydroisomerization of at least one $C_4$–$C_5$ n-paraffin, i.e., n-butane and/or n-pentane, in a single step.

Isobutene is a highly important compound in the petrochemicals industry. A large number of manufacturing processes use isobutene as a starting material, for example in the synthesis of methyltertiobutyl ether which is an additive for petrol formulations, in methacrylonitrile synthesis or in polymer synthesis.

The current main commercial route for producing isobutene is a two-step process starting from n-butane. The n-butane can, for example, be isomerised to isobutane in a first step (see, for example, French patent application FR-A-2 695 635), the isobutane then being dehydrogenated to isobutene in a second step (see, for example, European patent application EP-A-0 559 509). Anther route to the production of isobutene from n-butane is to dehydrogenate n-butane to n-butene in a first step then to isomerise the n-butene to isobutene. The catalysts, operating conditions, and separation techniques used for these different steps are generally different, meaning that the two steps must be carried out in two separate reactors, meaning high costs for the production of isobutene from n-butane.

Direct transformation of n-butane to isobutene thus has a certain advantage over two-step isobutene preparation processes. The problems which are generally encountered during this type of transformation are firstly, the low yield and secondly, the concomitant production of hydrogenolysis and/or cracking compounds as well as aromatic products. Finally, the loss of activity due to coating of the active surface by hydrocarbon deposits necessitates frequent regeneration of the catalyst.

A certain number of catalysts have already been mentioned for use in direct transformation of n-butane to isobutene. These catalysts generally comprise zeolite materials such as borosilicates (U.S. Pat. No. 4,433,190, U.S. Pat. No. 4,550,091), ZSM type aluminosilicates (EP-A-0 042 252), or zincoaluminates (U.S. Pat. No. 4,962,266), the material being used alone or in the presence of at least one group III metal (EP-A-0 042 252).

Other catalysts have been proposed, among them chromium, zirconium, niobium or tantalum oxides (EP-A-0 192 059) and catalysts containing a support such as alumina, at least one group VIII metal such as platinum, silicon and optionally tin and/or indium (GB-A-2 246 524).

The present invention concerns, in the dehydroisomerisation of at least one $C_4$–$C_5$ n-paraffin, preferably n-butane, the use of a catalyst comprising a refractory oxide based support such as alumina, at least one precious metal from group VIII, preferably platinum or palladium, more preferably platinum, at least one element from group IVb such as titanium or zirconium, preferably titanium, optionally at least one element from the group formed by germanium, tin, lead, rhenium, tungsten and indium, preferably tin, and optionally at least one halogen, preferably chlorine. The present invention also concerns the regeneration of the catalyst.

The use of the invention thus concerns the dehydroisomerisation of at least one $C_4$–$C_5$ n-paraffin, i.e., the transformation of said n-paraffin to a branched olefin.

The present invention preferably concerns, in the dehydroisomerisation of at least one $C_4$–$C_5$ n-paraffin, preferably n-butane, the use of a catalyst comprising a refractory oxide based support such as alumina, at least one precious metal from group VIII, preferably platinum or palladium, more preferably platinum, at least one element from group IVB (titanium or zirconium), optionally at least one element from the group formed by germanium, tin, lead, rhenium, tungsten and indium, preferably tin, and optionally at least one halogen, such as chlorine. The present invention also concerns the regeneration of the catalyst.

The present invention also concerns the regeneration of the catalyst following its deactivation after a long period of use.

The specific surface area of the refractory oxide based support, preferably an alumina, is advantageously generally between 10 and 500 $m^2/g$, preferably between 50 and 450 $m^2/g$, and its pore volume is generally between 0.4 and 0.8 $cm^3/g$.

The concentration of precious metal from group VIII in the catalyst of the invention, preferably of platinum or palladium, more preferably of platinum, is between 0.1% and 5% by weight, preferably between 0.2% and 0.7% by weight. The concentration of group IVB element in said catalyst is generally between 0.005% and 0.2% by weight. When the catalyst used in accordance with the invention comprises at least one metal from the group formed by geranium, tin, lead, rhenium, tungsten and indium, preferably tin, the concentration of said metal in said catalyst is generally between 0.1% and 5% by weight. When the catalyst used in accordance with the invention comprises at least one halogen, preferably chlorine, the concentration of the halogen in the catalyst is generally, by weight, generally from about 0.7 to 6% preferably from about 0.8 to 6%, and especially about 0.9 to 3%.

Preferably, the catalyst used in accordance with the invention comprises an alumina based support, generally in the form of spherules, and platinum. More preferably, the catalyst used in accordance with the invention comprises an alumina based support, platinum and titanium. More preferably, the catalyst used in accordance with the invention comprises an alumina based support, platinum, titanium, tin and chlorine.

The catalyst used in accordance with the invention can be prepared using techniques which are well known to the skilled person. Nevertheless, same details will be given below.

When using the preferred catalyst comprising an alumina based support, at least one group VIII precious metal, preferably platinum, and at least one group IVB element, preferably titanium, commercial aluminas can be used to prepare the catalyst. These are preferably activated, and preferably selected from the group formed by eta and gamma aluminas, with a low alkali content, for example containing less then 0.1% by weight of sodium. The catalyst is generally prepared by adding, in a preparation step for the modified support (i.e., an alumina based support comprising at least one group IVB metal, preferably titanium), 0.05% to 1%, preferably 0.085% to 0.5%, of an oxide of said group IVB element, preferably titanium dioxide, to the support. Any suitable addition method can be used. The compound of said group IVB element, preferably titanium, may, for example, be dissolved in a solution containing the aluminium compound and the alumina precipitation conditions can be adjusted so that the hydroxide of the group IVB element, preferably titanium, coprecipitates. It is also possible to add at least one compound of said group IVB element, preferably titanium, preferably selected, for example when the group IVB element is titanium, from the group formed by titanium dioxide in the rutile and octahedrite forms, sub-oxides TiO and $Ti_2O_3$, titanic acids, alkaline, alkaline-earth and ammonium titanates, and soluble and insoluble, organic and inorganic titanium salts, to a hydrated alumina in gel form (aluminium α-trihydrate, β-trihydrate or α-monohydrate). It is also possible to start with a formed alumina based support and impregnate it with an organic or inorganic salt solution of said group IVB element, preferably titanium; in general, the group IVB element, preferably titanium, can be added before, during or after forming the catalyst support.

In a first preferred preparation method for the modified support, when the group IVB element is titanium, at least one organic titanium compound, for example tetraethoxytitanium, is added to an organic solution (for example an alcoholic solution) of at least one organic aluminium compound (for example an alkoxyaluminium such as aluminium isopropylate), and the solution obtained is hydrolysed. In this case, it is also possible to add the titanium in the form of a readily hydrolysable inorganic compound such as titanium tetrachloride $TiCl_4$.

In a second preferred method of preparing the modified support, when the group IVB element is titanium, specific quantities of an organic titanium based compound, for example an alkoxytitanium such as tetraethyltitanium and/or an inorganic titanium compound (for example titanium trichloride) is added during the Ziegler synthesis of a polyalkoxyaluminium, by the reaction of an alkylaluminium (for example triethylaluminium), ethylene, and at least one of the above titanium compounds. Polymerisation and subsequent oxidation produces the above polyalkoxyaluminium, and hydrolysis produces polyols and the hydrated alumina containing the titanium.

It has been experimentally shown that the two preferred titanium impregnation methods described above produced a particularly high dispersion of titanium ions in the alumina matrix, after hydrolysis of the alkoxyaluminium or the polyalkoxyaluminium. When the support is in the form of spherules or extrudates, for example, these preferred titanium impregnation methods produce a $TiO_2$ concentration which is uniform from one spherule to another or from one extrudate to another; if the desired average concentration is C%, the concentration C from one spherule to another or one extrudate to another remains, when using the preferred methods of the invention, generally within C±5% by weight of this concentration, and even within C±3% by weight. Even more improved results have been obtained using modified catalyst supports containing, in particular, 0.06% to 0.15% of $TiO_2$, the titanium concentration in the support being measured using X-ray fluorescence.

The support obtained is then dried at a temperature of between 100° C. and 130° C., then optionally calcined in air at a temperature of between 400° C. and 800° C., preferably between 450° C. and 750° C., for a period of between 1 and 5 hours. It can then advantageously be steam treated at a temperature of between 120° C. and 700° C., preferably between 300° C. and 700° C., at a partial pressure of steam of more than 50 kPa, preferably between 60 and 100 kPa, for a period of between 0.5 and 120 hours, preferably between 1 and 100 hours.

The precious metal from group VIII, preferably platinum, is introduced using any technique known to the skilled person. The precious metal can, for example, be introduced using impregnation techniques using aqueous or organic solutions of a precursor of said precious metal, the precursor being, for example, an inorganic compound, for example when the precious metal is platinum, hexachloroplatinic acid, platinum tetramine dihydroxide, platinum tetramine chloride or an organometallic compound such as platinum bis π allyl, or platinum bis acetylacetonate. Following introduction of the precious metal, the catalyst can optionally be dried, calcined at a temperature of between 300° C. and 700° C., preferably between 350° C. and 550° C., and/or reduced at a temperature of between 300° C. and 700° C., preferably between 350° C. and 550° C.

When the catalyst used in accordance with the invention comprises at least one element from the group formed by germanium, tin, lead, rhenium, tungsten and indium, preferably tin, the element can, for example, be incorporated into the support by impregnation using a suitable aqueous or organic solution, comprising a salt or a compound of said element such as a chloride, acetate, tartrate or alkoyl compound.

The dehydroisomerisation reaction of at least one $C_4$–$C_5$ n-paraffin, preferably n-butane, is carried out in a dehydroisomerisation zone, by passing a feed comprising at least one $C_4$–$C_5$ n-paraffin, preferably n-butane, over the catalyst at high temperature in the dehydroisomerisation zone. Before reaction, the catalyst can optionally be reduced. In general the dehydroisomerisation reaction is carried out at a temperature of between 250° C. and 600° C., preferably between 400° C. and 600° C., at a total pressure of between 10 and 5000 kPa, preferably between 30 and 200 kPa, with a hydrogen/hydrocarbon molar ratio of between 0 and 10 and with a volume flow rate, expressed as the gaseous volume of feed per hour per volume of catalyst, of between 30000 and 75 $h^{-1}$, preferably between 15000 and 200 $h^{-1}$.

The catalyst used in accordance with the invention can be regenerated after a period of use. The catalyst is regenerated by controlled combustion of the hydrocarbon species present on the catalyst. Combustion is carried out under conditions which are known to the skilled person, generally by slowly heating the catalyst in the presence of a gas containing oxygen to a temperature of between 350° C. and 500° C. When the catalyst used in accordance with the invention comprises at least one halogen, preferably chlorine, regeneration can also include, after the coke combustion step, a catalyst oxyhalogenation step, preferably an oxychlorination step, consisting of introducing at least one halogenated derivative, i.e., at least one halogen and/or halogenated compound, preferably at least chlorine and/or a chlorine compound, at the end of the combustion step. The quantity of halogen used is between 0.1 and 2 g of halogen per 100 g of catalyst. In such an oxyhalogenation reaction, the temperature is generally between 350° C. and 650° C. and the pressure is generally between 101 and 1500 kPa.

The following examples illustrate the invention without in any way limiting its scope.

EXAMPLE 1

Preparation of Catalyst A

A commercial gamma alumina support with a surface area of 200 $m^2/g$ and a pore volume of 0.6 $cm^3/g$, was impregnated with 0.1% of titanium starting from titanium oxalate decahydrate in aqueous solution, then dried at 100° C. for 2 hours and calcined at 600° C. for 2 hours. The support was then steam treated at 560° C. for 20 hours at a partial pressure of steam of 80 kPa. 0.6% of platinum was then deposited using prior art techniques:

500 $cm^3$ of an aqueous solution of hydrochloric acid was added to 100 g of support. This was left in contact for three hours, drained, and dried for 1 hour at 120° C. This chlorine-containing product was then impregnated with platinum by adding 150 cm³ of a hexachloroplatinic acid solution to the solid. The platinum concentration in this solution was 4.05 g per liter. This was left in contact for 6 hours, dried for 1 hour at 120° C. and calcined for 2 hours at 530° C.

The product obtained, catalyst A, contained 0.6% of platinum, 0.1% of titanium and 1.2% of chlorine (weight %).

EXAMPLE 2

Preparation of Catalyst B

The support used in this Example was equivalent to the support described in Example 1. Platinum and tin were deposited using prior art techniques.

500 cm³ of an aqueous solution of hydrochloric acid was added to 100 g of support. This was left in contact for 3 hours, drained, and dried for 1 hour at 120° C. This chlorine-containing product was then impregnated with platinum and tin by adding 150 cm³ of a solution of hexachloroplatinic acid and stannic acid to the solid. The platinum concentration in this solution was 4.05 g per liter, and the tin concentration was 3.04 g per liter. This was left in contact for 6 hours, dried for 1 hour at 120° C. and calcined for 2 hours at 530° C.

The product obtained, catalyst B, contained 0.6% of platinum, 0.1% of titanium, 0.3% of tin and 1.2% of chlorine (weight %).

EXAMPLE 3

Preparation of Catalyst C

The catalyst used in this Example differed from that of Example 1 only in that the commercial gamma alumina support was not impregnated with titanium. All the subsequent steps of the preparation were identical to those of Example 1.

The product obtained, catalyst C, contained 0.6% of platinum and 1.2% of chlorine (weight %).

EXAMPLE 4

Preparation of Catalyst D

A catalyst was prepared from 300 g of almumina support impregnated with titanium as described in Example 1. The platinum was then introduced by adding 1500 cm³ of an organic (toluene) solution of platinum bis acetylacetonate containing a total of 1.8 g of platinum. This was left in contact for 2 hours, filtered then dried for 1 hour at 120° C., then calcined for 4 hours at 400° C. The product obtained, catalyst D, contained 0.6% of platinum and 0.1% of titanium.

EXAMPLE 5

Comparison of the Performances of the Different Catalysts in the Dehydroisomerisation of n-Butane 1 g of the catalyst to be tested was placed in a quarts up-flow reactor with an internal diameter of 20 mm operated at atmospheric pressure. The catalyst was first reduced at 350° C. in a hydrogen stream of 1 liter per hour for two hours. After this reduction, the temperature was raised to 530° C. A gaseous mixture containing n-butane, hydrogen and nitrogen was injected. The hydrogen-n-butane molar ratio was 1. The nitrogen/hydrogen ratio was 0.5. The gas flow rate, expressed as the volume of n-butane per hour per liter of catalyst, was 2750 h$^{-1}$. The temperature was then stabilised at 550° C. The results of the analysis of gaseous samples taken after 4 hours of operation are shown in Table 1.

TABLE 1

| Catalyst | Conversion (%) | Yield (weight %) | |
|---|---|---|---|
| | | i-butene | butenes |
| A | 52 | 21 | 59 |
| B | 90 | 28 | 71 |
| C | 37 | 15 | 52 |
| D | 27 | 3 | 27 |

EXAMPLE 6

Regeneration of Used Catalysts A and B

After use of catalyst A or B for 12 hours under the conditions of Example 5, catalyst A or B was regenerated. In this regeneration procedure, catalyst A or B was brought to 200° C. in nitrogen, then treated in diluted air at a temperature of between 200° C. and 500° C. to burn off the hydrocarbon compounds present on the catalyst. Catalyst A or B was then steam treated at 560° C. for 20 hours at a partial pressure of steam of 0.8 bar.

After regeneration, the performances of the regenerated catalysts A and B were evaluated under the conditions of Example 5. The performances of such regenerated systems are shown in Table 2.

TABLE 2

| Catalyst | Conversion (%) | Yield (weight %) | |
|---|---|---|---|
| | | i-butene | butenes |
| A | 52 | 21 | 59 |
| A-regenerated | 30 | 19 | 53 |
| B | 90 | 28 | 71 |
| B-regenerated | 87 | 29 | 73 |

The preceding examples can be repeated with similar success by substituting the generically or specifically described reactants and/or operating conditions of this invention for those used in the preceding examples.

The entire disclosure of all applications, patents and publications, cited above and below, and of corresponding French application 94/05.294, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

We claim:

1. A process for the simultaneous dehydroisomerization of at least one n-$C_4$–$C_5$ paraffin to produce a $C_4$–$C_5$ isolefin, said dehydroisomerization being carried out in a dehydroisomerization zone under dehydroisomerization conditions by passing a gaseous hydrocarbon feed containing at least one n-$C_4$–$C_5$ paraffin over a catalyst, the improvement wherein said catalyst comprises a refractory oxide based support, at least one precious metal from group VIII, at least one element from group IVB selected from the group consisting of titanium and zirconium; at least one metal selected from the group consisting of germanium, tin, lead, rhenium, tungsten and indium; and a halogen, and wherein the dehydroisomerization is conducted in a single step.

2. A process according to claim 1, said dehydroisomerization being conducted at a temperature of between 250° C. and 600° C., at a total pressure of between 10 and 5000 kPa, with a hydrogen/hydrocarbon molar ratio of between 0 and 10 and with a volumetric flow rate, expressed as the volume of gaseous feed per hour per volume of catalyst, of between 30000 and 75 $h^{-1}$.

3. A process according to claim 1 wherein said precious metal from group VIII is platinum or palladium.

4. A process according to claim 1 wherein said precious metal from group VIII is platinum.

5. A process according to claim 1, wherein said halogen is chlorine.

6. A process according to claim 5, wherein the content, by weight, of chlorine in the catalyst is about 0.7 to 6%.

7. A process according to claim 5, wherein the content, by weight, of chlorine in the catalyst is about 0.9 to 3%.

8. A process according to claim 1, wherein said metal is tin.

9. A process according to claim 1 wherein said n-paraffin is n-butane.

10. A process according to claim 1 wherein the support is alumina.

* * * * *